US006782328B2

(12) United States Patent
Lovegren et al.

(10) Patent No.: US 6,782,328 B2
(45) Date of Patent: Aug. 24, 2004

(54) MEASUREMENT OF CONCENTRATION OF MATERIAL IN A PROCESS FLUID

(75) Inventors: Eric R. Lovegren, Big Lake, MN (US); Mark S. Schumacher, Minneapolis, MN (US); James A. Johnson, Savage, MN (US); Kurt C. Diede, Apple Valley, MN (US)

(73) Assignee: Rosemount Inc., Eden Prairie, MN (US)

( * ) Notice: Subject to any disclaimer, the term of this patent is extended or adjusted under 35 U.S.C. 154(b) by 167 days.

(21) Appl. No.: 10/046,647

(22) Filed: Oct. 29, 2001

(65) Prior Publication Data

US 2002/0177961 A1 Nov. 28, 2002

Related U.S. Application Data

(63) Continuation-in-part of application No. 09/235,114, filed on Jan. 21, 1999, now Pat. No. 6,477,474.

(51) Int. Cl.[7] .............................................. G06F 19/00
(52) U.S. Cl. ...................................... 702/50; 324/642
(58) Field of Search ........................... 702/50; 324/642, 324/633, 693, 636; 73/863.02

(56) References Cited

U.S. PATENT DOCUMENTS

| | | | |
|---|---|---|---|
| 3,665,466 A | 5/1972 | Hibbard | .................... 343/12 R |
| 3,812,422 A | 5/1974 | DeCarolis | .................. 324/58.5 |
| 3,832,900 A | 9/1974 | Ross | ........................ 73/290 R |

(List continued on next page.)

FOREIGN PATENT DOCUMENTS

| | | |
|---|---|---|
| EP | 0 372 843 A1 | 6/1990 |
| EP | 0 882 956 A2 | 6/1997 |
| EP | 0 882 957 A2 | 12/1998 |
| JP | 2000241364 * | 9/2000 |
| WO | WO 00/43806 | 7/2000 |
| WO | WO 01/36951 A2 | 5/2001 |

OTHER PUBLICATIONS

"Notification of Transmittal of the International Search Report or the Declaration" for PCT/US02/31951.
"Micropower Impulse Radar Technology and Applications" by J. Mast et al., *Lawrence Livermore National Laboratory*, UCRL–ID–130474, Apr. 15, 1998.
"Reflex–Radar Gauging and level measurement for liquids, interface and granular materials", KROHNE Technical Data, Dec. 1996.
"Radar Level Technology Offers Accurate, Noncontact Measurements" by F. Fitch, I&CS, Jan. 1996, pp. 27–30.
"Novel Methods of Measuring Impurity Levels in Liquid Tanks" by Matthias Weib, XP–000767081, *IEEE MTT–S Digest*, pp. 1651–1654, Aug. 6, 1997.
"Determination of Volumetric Water Content in Lossy Geophysical Media Using Time Domain Reflectometry" by B. Oswald et al., *Laboratory for Electromagnetic Fields and Microwave Electronics, Swiss Federal Institute of Technology*, pp. 2054–2057, 1997.
"Measurement of Dielectric Properties of Materials by Using Time Domain Reflectometry" by R. Nozaki et al., CH2735–9/90/000–0263, 1999, pp. 263–269.
"Continuous Measurement of Cerebral Water Content by Time Domain Reflectometry" by G.G. Kramer et al., IEEE Engineering in Medicine and Biology Societ, vol. 14, No. 4, 1991, pp. 1593–1594.

*Primary Examiner*—John Barlow
*Assistant Examiner*—Xiuqin Sun
(74) *Attorney, Agent, or Firm*—Westman, Champlin & Kelly, P.A.

(57) ABSTRACT

An apparatus for measuring concentration of a material in a process fluid includes an antenna configured to contact the process fluid and a pulse generator coupled to the antenna to generate a microwave transmit pulse through the antenna. A pulse receiver receives a reflected pulse from the antenna and the concentration of the material is calculated as a function of the reflected pulse.

19 Claims, 15 Drawing Sheets

U.S. PATENT DOCUMENTS

| | | | |
|---|---|---|---|
| 3,853,005 A | 12/1974 | Schendel | 73/290 R |
| 3,900,260 A | 8/1975 | Wendt | 356/5 |
| 3,995,212 A | 11/1976 | Ross | 324/58.5 B |
| 4,044,355 A | 8/1977 | Edvardsson | 343/14 |
| 4,161,731 A | 7/1979 | Barr | 343/14 |
| 4,196,385 A * | 4/1980 | Vestergaard et al. | 324/642 |
| 4,435,709 A | 3/1984 | Kipp | 343/14 |
| 4,489,601 A | 12/1984 | Rao et al. | 73/290 R |
| 4,786,587 A | 11/1988 | Kuwabara | 430/566 |
| 4,838,690 A | 6/1989 | Buckland et al. | 356/73.1 |
| 4,972,386 A | 11/1990 | Lau | 367/99 |
| 5,157,337 A | 10/1992 | Neel et al. | 324/632 |
| 5,313,168 A | 5/1994 | Ogawa | 324/663 |
| 5,327,139 A | 7/1994 | Johnson | 342/22 |
| 5,345,183 A | 9/1994 | Take | 324/663 |
| 5,365,178 A | 11/1994 | Van Der Pol | 324/644 |
| 5,440,310 A | 8/1995 | Schnreiner | 342/124 |
| 5,500,649 A | 3/1996 | Mowrey et al. | 342/22 |
| 5,599,449 A | 2/1997 | Gnamm et al. | 210/495 |
| 5,609,059 A | 3/1997 | McEwan | 73/290 R |
| 5,610,611 A | 3/1997 | McEwan | 342/89 |
| 5,656,774 A | 8/1997 | Nelson et al. | 73/290 |
| 5,659,321 A | 8/1997 | Burger et al. | 342/124 |
| 5,661,251 A | 8/1997 | Cummings et al. | 73/866.5 |
| 5,672,975 A | 9/1997 | Kielb et al. | 324/644 |
| 5,726,578 A | 3/1998 | Hook | 324/643 |
| 5,734,346 A | 3/1998 | Richardson et al. | 342/124 |
| 5,748,002 A * | 5/1998 | Scott et al. | 324/633 |
| 5,763,794 A * | 6/1998 | Marrelli | 73/863.02 |
| 5,811,677 A | 9/1998 | Cournance | 73/304 R |
| 5,835,053 A | 11/1998 | Davis | 342/22 |
| 5,864,239 A * | 1/1999 | Adams et al. | 324/636 |
| 5,898,308 A | 4/1999 | Champion | 324/643 |
| 6,130,637 A | 10/2000 | Meszaros et al. | 342/124 |
| 6,166,681 A | 12/2000 | Meszaros et al. | 342/124 |
| 6,184,818 B1 | 2/2001 | Meinel | 342/124 |
| 6,198,424 B1 | 3/2001 | Diede et al. | 342/22 |
| 6,614,238 B1 * | 9/2003 | Jean et al. | 324/639 |

* cited by examiner

MEASUREMENT OF CONCENTRATION OF MATERIAL IN A PROCESS FLUID

The present application is a Continuation-In-Part of and claims priority of U.S. patent application Ser. No. 09/235,114, filed Jan. 21, 1999, now U.S. Pat. No. 6,477,474, the content of which is hereby incorporated by reference in its entirety.

BACKGROUND OF THE INVENTION

The process control industry employs process variable transmitters to remotely monitor process variables associated with substances such as solids, slurries, liquids, vapors, and gasses in chemical, pulp, petroleum, pharmaceutical, food and other food processing plants. Process variables include pressure, temperature, flow, level, turbidity, density, concentration, chemical composition and other properties. A process variable transmitter can provide an output related to the sensed process variable over a process control loop to a control room, such that the process can be monitored and controlled.

The process control loop can be a two-wire, 4–20 mA process control loop. With such a process control loop, the energization levels are low enough that even under fault conditions the loop generally will not contain enough electrical energy to generate a spark. This is particularly advantageous in flammable environments. Process variable transmitters can sometimes operate on such low energy levels that they can receive all electrical power from the 4–20 mA loop. The control loop may also have digital signals superimposed on the two-wire loop according to a process industry standard protocol such as the HART® digital protocol.

Low power Time Domain Reflectometry radar (LPTDRR) instruments have been used to measure the level of process products (either liquids or solids) in storage vessels. In Time Domain Reflectometry, electromagnetic energy is transmitted from a source, and reflected at a discontinuity. The travel time of the received pulse is based on the media through which it travels. One type of LPTDRR is known as Micropower Impulse Radar (MIR), which was developed by Lawrence Livermore National Laboratory. LPTDRR level transmitters typically determine level (such as level of a fluid in a storage tank) as a function of the time of travel of microwave signals to and from an interface or surface of the product. However, this technology may be used to measure process variables other than level.

SUMMARY OF THE INVENTION

An apparatus for measuring concentration of a material in a process fluid includes an antenna configured to contact the process fluid and a pulse generator coupled to configure the antenna to generate a microwave transmit pulse through the antenna. A pulse receiver receives a reflected pulse from the antenna and the concentration of the material is calculated as a function of the reflected pulse.

DETAILED DESCRIPTION OF THE PREFERRED EMBODIMENTS

The present invention uses microwave radiation to measure the concentration of a material, or materials, in a process fluid. In particular, the invention recognizes that the concentration of a material can change the dielectric constant of the process fluid. The change in reflected microwave radiation can be correlated to the concentration, absolute or relative, of a material within the process fluid.

Figure 1:
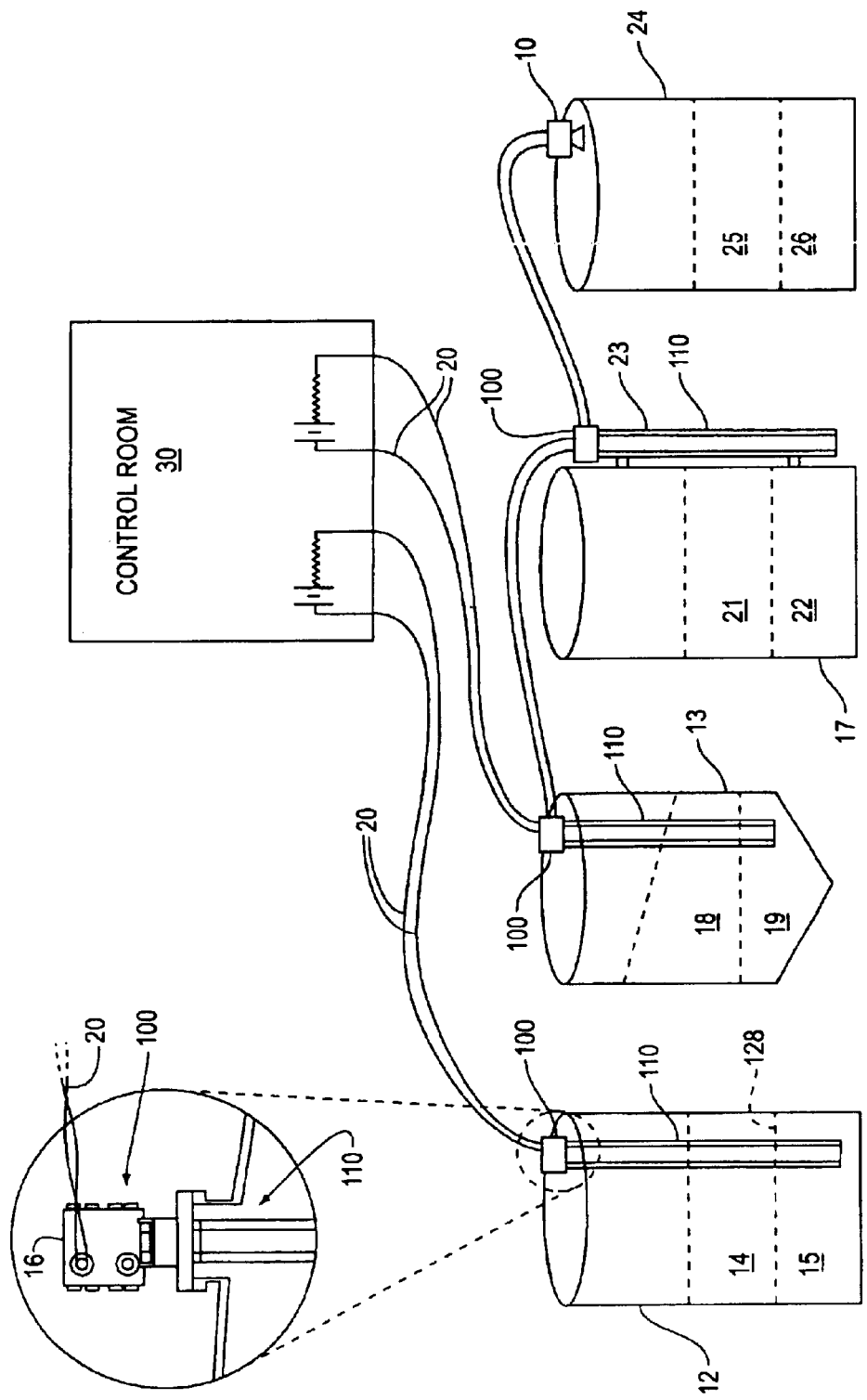
FIG. 1 is a diagram of a process control system illustrating the environment of embodiments of the invention.

FIG. 1 is a diagram illustrating level transmitters 100 operating in the environment of being mounted to storage tanks 12, 13, 17, 24 containing at least one product. As illustrated, tank 12 contains first product 14 positioned on top of second product 15. Transmitters 100 include housings 16 and terminations 110. Transmitters 100 are coupled to process control loops 20, and transmit information related to dielectric constants and/or heights of the process products over loops 20 to control room 30 (which is modeled as voltage sources and resistances) or to other devices (not shown) coupled to process control loops 20. Loops 20 are sources of power for transmitters 100 and can use any process industry standard communications protocol such as 4–20 mA, Foundation™ Fieldbus, or HART®. As low power radar transmitters, transmitters 100 can be completely powered by energy received over a 4–20 mA process control loop.

FIG. 1 illustrates various applications in which radar dielectric constant measurement is useful. For example, process products 14 and 15 in tank 12 are fluids, while process products 18 (shown having a given angle of repose)

and 19 in tank 13 are solids. Process products 21 and 22 in tank 17 are fluids the levels of which are communicated to tube 23 into which one of terminations 110 extends. Further, tank 24 is shown containing products 25 and 26, and having a radiative-type termination mounted on top of tank 24. Although tanks 12, 13, 17 and 24 are shown in FIG. 1, the embodiments of the invention may be practiced without tanks such as in a lake or reservoir.

Figure 2:
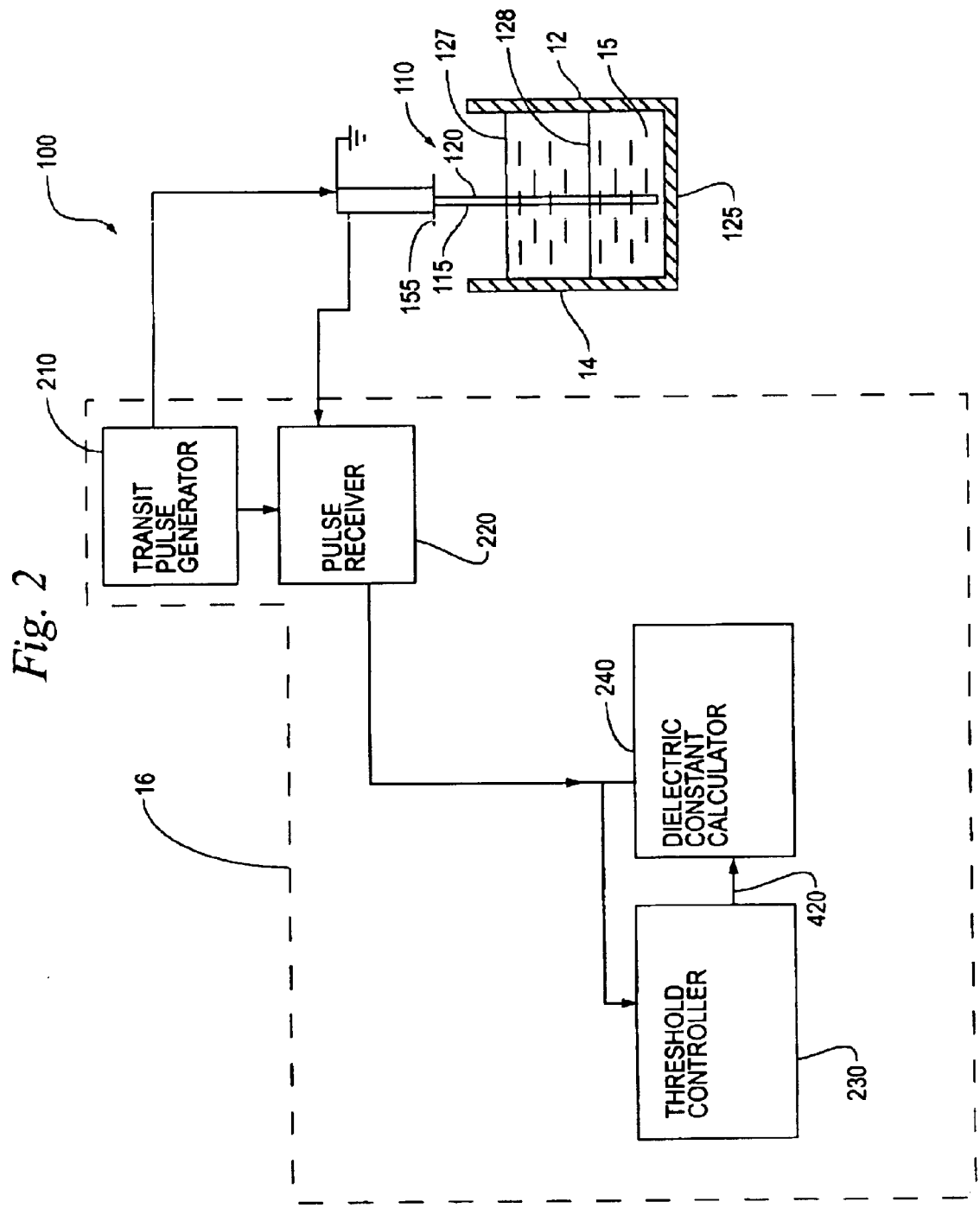
FIG. 2 is a block diagram illustrating circuitry of a radar level transmitter in accordance with an embodiment of the invention.
Figure 3:
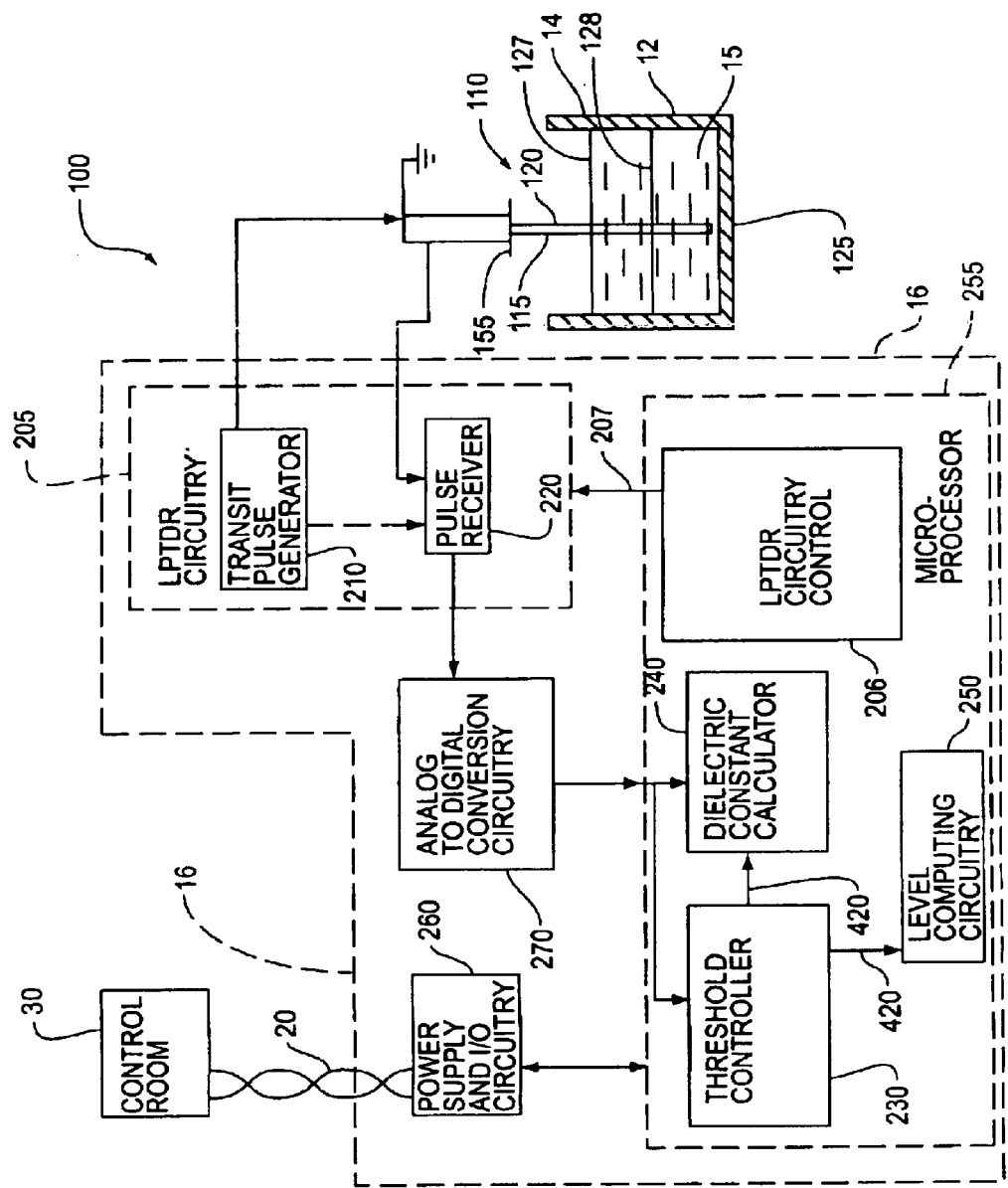
FIG. 3 is a block diagram illustrating circuitry of a radar level transmitter in accordance with an alternate embodiment of the invention.
Figure 4:
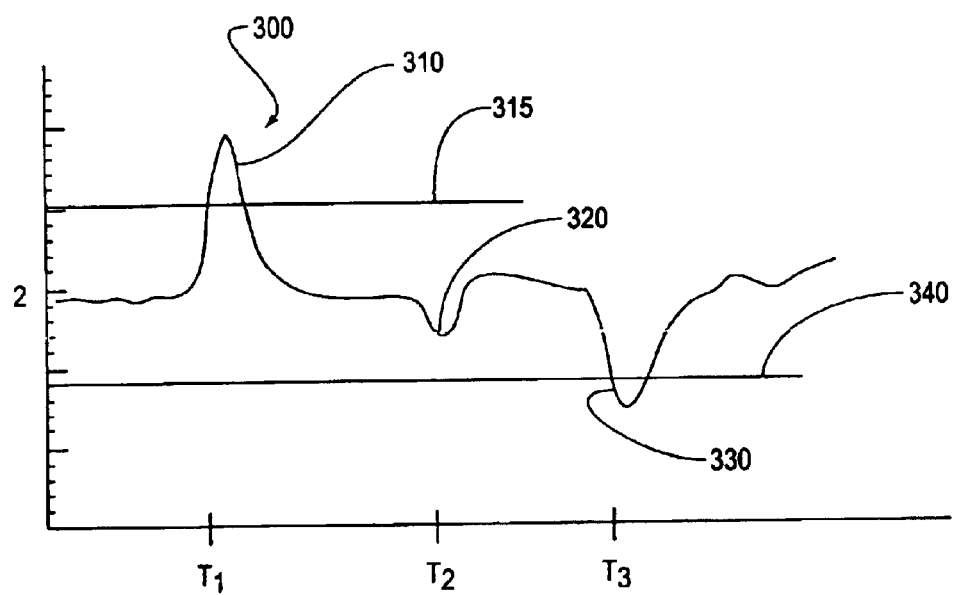
FIGS. 4 and 5 are plots illustrating Low Power Time Domain Reflectometry (LPTDRR) equivalent time waveform controllable thresholds.
Figure 5:
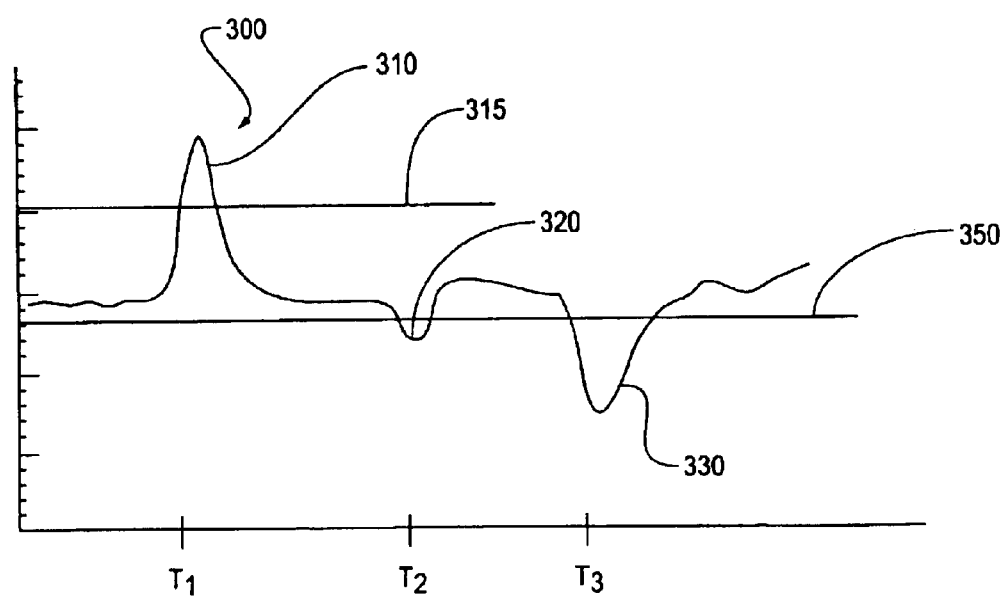

FIGS. 2 and 3 are block diagrams of a transmitter 100. FIGS. 4 and 5 are plots of equivalent time Low Power Time Domain Reflectometry Radar (LPTDRR) transmit/receive waveforms illustrating controllable threshold detector aspects of the invention. Within housing 16, transmitter 100 includes LPTDRR circuitry 205 (shown in FIG. 3), LPTDRR circuitry controller 206 (shown in FIG. 3) and dielectric constant calculator 240. Controller 206 controls LPTDRR circuitry 205 via connections 207 in order to determine a parameter which is proportional to the dielectric constant of product 14 in tank 12. Dielectric constant calculator 240 calculates the dielectric constant of product 14 as a function of the determined parameter. LPTDRR circuitry 205 can include transmit pulse generator 210 and pulse receiver 220.

Transmitter 100 also includes threshold controller 230 and optionally level computing circuitry 250 (shown in FIG. 3). Threshold controller 230 can be a component of LPTDRR circuitry 205. Threshold controller 230, dielectric constant calculator 240, level computing circuitry 250 and LPTDRR controller 206 can be implemented in microprocessor 255 as shown in FIG. 3. However, discrete circuitry for any of these functions can be used. In embodiments in which these functions are embodied in microprocessor 255, transmitter 100 includes analog-to-digital converter 270. Transmitter 100 can also include power supply and input/output circuitry 260 (as shown in FIG. 3) for powering transmitter 100 with power received over loop 20, and for communicating over loop 20. Such communication can include transmitting information related to the process product over loop 20. The power supply circuitry can be adapted to provide the sole source of power for transmitter 100 from power received over loop 20.

Microwave termination 110 can be of the type which are well known in the level transmitter art and can be any appropriate transmission line, waveguide or antenna. A transmission line is a system of material boundaries forming a continuous path from one place to another and capable of directing transmission of electromagnetic energy along this path. In some embodiments, termination 110 is a twin lead antenna having leads or conductors 115 and 120 connected at bottom region 125 and extendable into products 14 and 15 in tank 12, and optionally having launch plate 155. Termination 110 can also be a monopole, coaxial, twin-line, single-line, microstrip, or radiative horn termination and can have any appropriate number of leads.

Transmit pulse generator 210 is preferably a low power microwave source coupled to termination 110. Under the control of controller 206, generator 210 generates a microwave transmit pulse or signal which is transmitted along termination 110 into products 14, 15. The transmit pulse can be at any of a wide range of frequencies, for example between about 250 MHz and about 20 GHz or more. In one embodiment the frequency of the transmit pulse is about 2.0 GHz. Fiducial pulse 310 of equivalent time waveform 300 (shown in FIGS. 4 and 5) can be created at launch plate 155 or by other mechanisms to designate the beginning of a transmit/receive cycle. A first portion of the transmit pulse microwave energy transmitted along leads 115 and 120 is reflected at first product interface 127 between air and product 14. A second portion of the transmit pulse microwave energy is reflected at interface 128 between product 14 and product 15. If tank 12 contains only product 14, but not product 15, interface 128 is typically the bottom of the termination or tank. In FIGS. 4 and 5, pulse 320 of equivalent time waveform 300 represents microwave energy reflected at interface 127 between air and product 14, while pulse 330 represents microwave energy reflected at interface 128. Those skilled in the art will recognize that the waveforms shown in FIGS. 4 and 5 can be inverted without departing from the spirit and scope of the invention. In general, if product 14 has a dielectric constant which is less than the dielectric constant of product 15, the amplitude of pulse 330 can be larger than pulse 320.

Pulse receiver 220 is a low power microwave receiver coupled to termination 110. Receiver 220 receives the first reflected wave pulse corresponding to reflection of the first portion of the transmit pulse at the first product interface 127 (represented by pulse 320 in FIGS. 4 and 5). Receiver 220 also receives the second reflected wave pulse corresponding to reflection of the second portion of the transmit pulse at the second product interface 128 (represented by pulse 330 in FIGS. 4 and 5). Using a known low power time domain reflectometry radar sampling technique, pulse receiver 220 produces as an output equivalent time LPTDRR waveform 300.

Threshold controller 230 receives waveform 300 as an input. In embodiments in which threshold controller 230 and dielectric constant calculator 240 are embodied in microprocessor 255, analog-to-digital circuitry 270 digitizes waveform 300. Threshold controller 230 generates thresholds 315, 340 and 350 for detection of fiducial pulse 310 and thus time $T_1$ at which pulse 310 was received, detection of reflected wave pulse 320 and thus time $T_2$ at which pulse 320 was received, and detection of reflected wave pulse 330 and thus time $T_3$ at which pulse 330 was received. Threshold value 315 used to detect fiducial pulse 310 can be a predetermined constant voltage, or can be automatically determined as a function of the peak amplitude of pulse 310 in a known manner. Threshold controller 230 provides receive pulse threshold 340 shown in FIG. 4 at a level which is surpassed by pulse 330. Threshold controller 230 provides receive pulse threshold 350 shown in FIG. 5 at a level which is surpassed by pulse 320. Threshold controller 230 provides as an output to dielectric constant calculator 240 and to circuitry 250, receive pulse output information based upon detection of reflected wave pulses 320 and/or 330.

Figure 6:
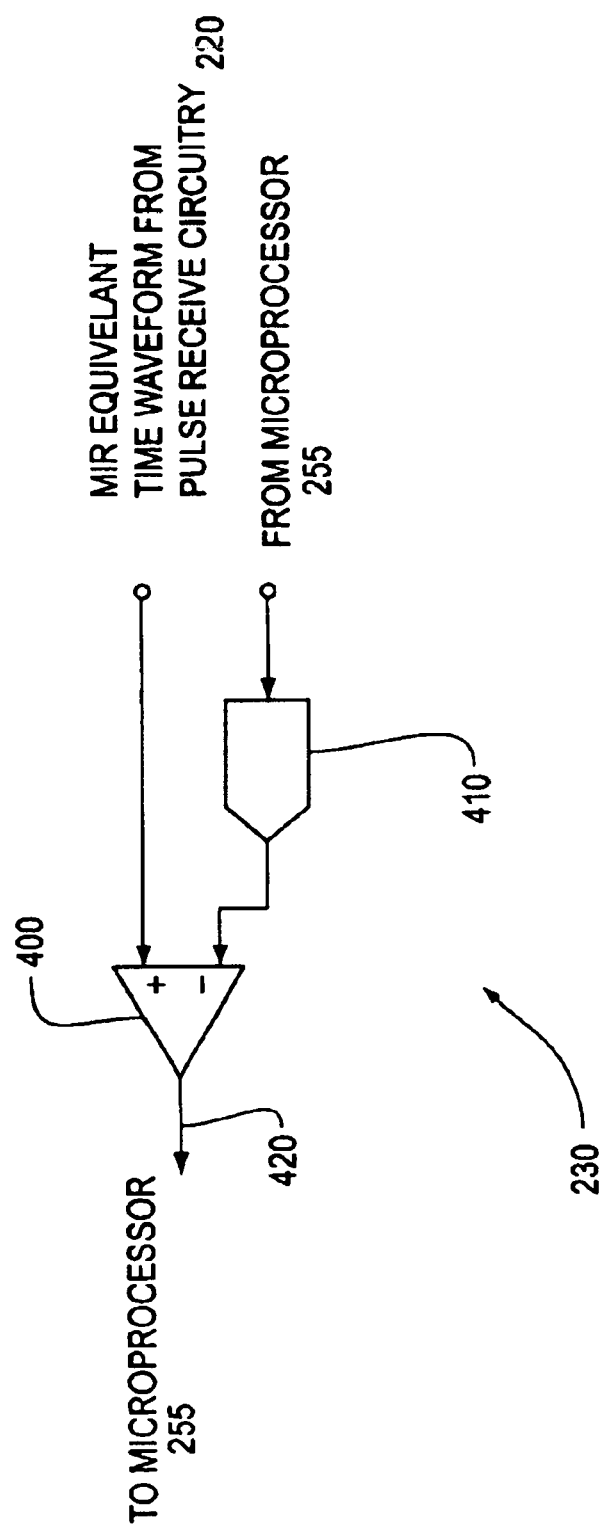
FIG. 6 is a schematic diagram of a controllable receive threshold circuitry in accordance with an embodiment of the invention.

FIG. 6 illustrates a portion of threshold controller 230, implemented in discrete circuitry, which generates controllable thresholds such as thresholds 340 and 350. Threshold controller 230 includes comparator 400, having a first input from receiver 220 waveform 300 containing receive pulses 320 and 330. As a second input, comparator 400 receives the controllable analog threshold voltage which is provided from the output of digital-to-analog converter 410. Converter 410 receives a digital input from microprocessor 255 representative of the desired threshold. The output 420 of comparator 400 is provided to dielectric constant calculator 240 and level computing circuitry 250 as an indication of the times that pulses 320 and 330 are received. During a first scan cycle in which waveform 300 is generated, converter 410 is controlled to provide threshold 350 for detection of pulse 320. During a subsequent scan cycle, converter 410 is controlled to provide threshold 340 for detection of pulse 330. The thresholds can be used to detect the times of receipt of the reflected wave pulses. The thresholds can also be controlled to determine the amplitudes of the reflected wave pulses.

Dielectric constant calculator 240 in FIG. 2 is coupled to threshold controller 230 and is adapted to calculate a dielectric constant of first product 14 in tank 12 as a function of the receive pulse output information provided by threshold controller 230. Methods implemented by circuitry 240 in calculating the dielectric constant are discussed below in detail with reference to FIGS. 7–12.

The relationship between the distance traveled by a microwave signal and the time of travel is shown in Equation 1.

$$D = \left(\frac{1}{\sqrt{\varepsilon_R}}\right) C\left(\frac{T}{2}\right) \qquad \text{Eq. 1}$$

where:

T/2=one half of the travel time of the microwave pulse to and from the interface;
$\varepsilon_R$=the dielectric constant of the material through which the microwave pulse travels (for air, $\varepsilon_R$=1)
C=the speed of light; and
D=the distance traveled from the top of the termination to the interface.

Using this relationship, the dielectric constant of a material being measured can be calculated. The time of travel of a microwave is dependent upon the dielectric constant of the medium it is travelling through. The dielectric constant of the medium is proportional to the travel time according to the relationship shown in Equation 2.

$$\varepsilon_R \propto (A \cdot \text{Time})^2 \qquad \text{Eq. 2}$$

where:

Time=microwave travel time through medium; and
A=a proportionality constant.

Also, the amplitude of the pulse reflected off of an interface with a material is proportional to the dielectric constant of the material according to the relationship shown in Equation 3.

$$\varepsilon_R \propto \frac{V_R}{V_T} \qquad \text{Eq. 3}$$

where:

$V_R$=the amplitude of the reflected pulse; and
$V_T$=the amplitude of the transmitted pulse.

Using the relationships illustrated in Equations 2 and 3, independently or in combination, the dielectric constant(s) of one or more products or materials in a tank can be calculated.

Methods

Figure 7:
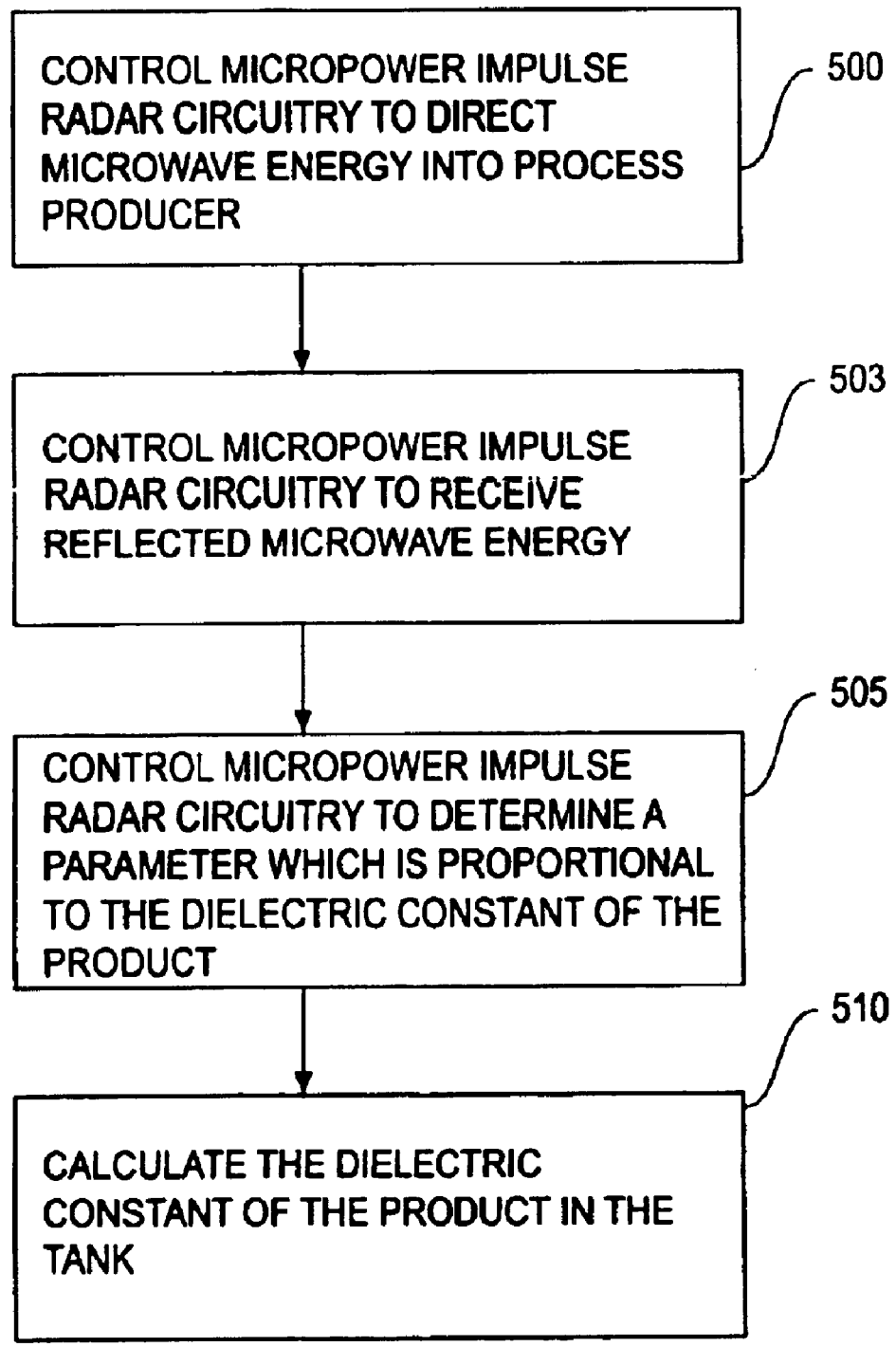
FIGS. 7, 9 and 12 are flow diagrams illustrating methods implemented by the microwave transmitter of FIG. 2.

A method of calculating the dielectric constant of product 14 is illustrated in FIG. 7. The method begins at block 500 with controlling the low power time domain reflectometry radar (LPTDRR) to direct microwave energy into the process product. At block 503, the LPTDRR circuitry is controlled to receive the reflected microwave energy. At block 505 the LPTDRR circuitry is controlled to measure a parameter which is proportional to the dielectric constant of product 14. Then, at block 510, the dielectric constant of product 14 is calculated as a function of the measured parameter using the relationships of Equation 2 and/or Equation 3.

Figure 8:
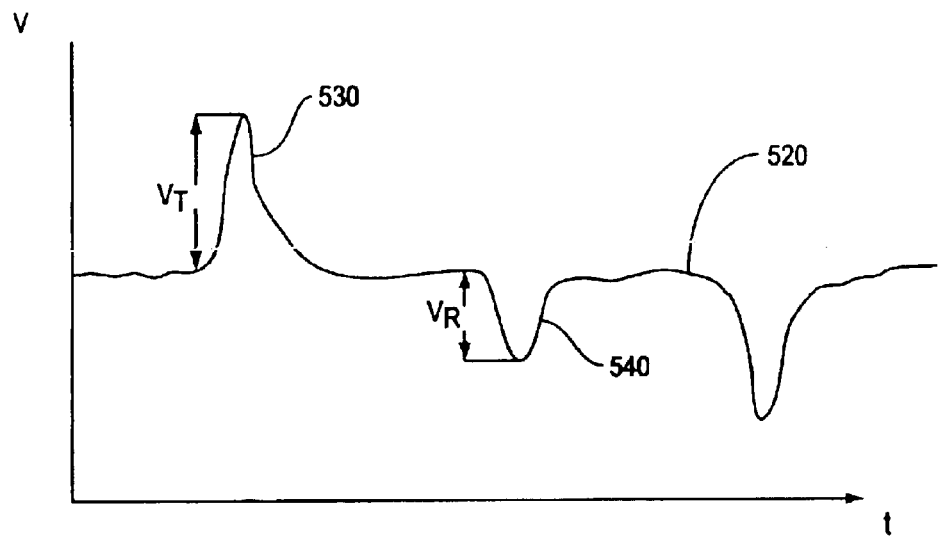
FIGS. 8, 10 and 11 are plots illustrating LPTDRR equivalent time waveforms.
Figure 9:
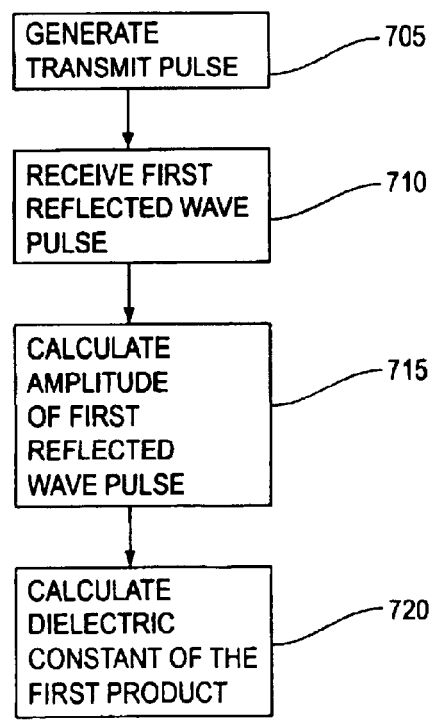

A first more particular method of calculating the dielectric constant of product 14 with the relationship of Equation 3 uses threshold controller 230 to more precisely measure the transmitted and reflected pulse amplitudes. The method is shown in the plot of FIG. 8, and is summarized in the flow diagram of FIG. 9. Those skilled in the art will recognize that the waveform shown in FIG. 8 can be inverted without departing from the spirit and scope of the invention.

The method begins at block 705 with generating a transmit pulse. The transmit pulse is transmitted along the termination into the products in the tank, and reflects off of surfaces 127 and 128. At block 710, the first reflected wave pulse 540 is received. The first reflected wave pulse corresponds to reflection of the first portion of the transmit pulse at the first product interface 127. After controlling LPTDRR circuitry 205 to receive the reflected wave pulse, at block 715 the amplitude of the first reflected wave pulse is calculated. The amplitude of the first reflected wave pulse is a parameter which is proportional to the dielectric constant of product 14.

At block 720, the dielectric constant of the first product is calculated as a function of the first reflected wave pulse. As shown in equivalent time LPTDRR waveform 520 of FIG. 8, the transmit pulse (represented by fiducial pulse 530) has a transmit amplitude $V_T$, while the receive pulse 540 has a receive amplitude $V_R$. Either by digitizing the equivalent time LPTDRR waveform 520 with analog-to-digital converter 270 and analyzing the digitized signal with microprocessor 255, or by using digital-to analog converter 410 to set comparator thresholds, the amplitude of the first reflected wave pulse is calculated, and the dielectric constant of first product 14 is calculated using Equation 3. Thus, the calculated parameter which is proportional to the dielectric constant of product 14 is typically a ratio between the amplitude of the first reflected wave pulse and the amplitude of the transmitted pulse. Controlling the LPTDRR circuitry includes controlling threshold controller 230 to adjust a threshold to calculate the amplitude of reflected wave pulse 540.

Figure 10:
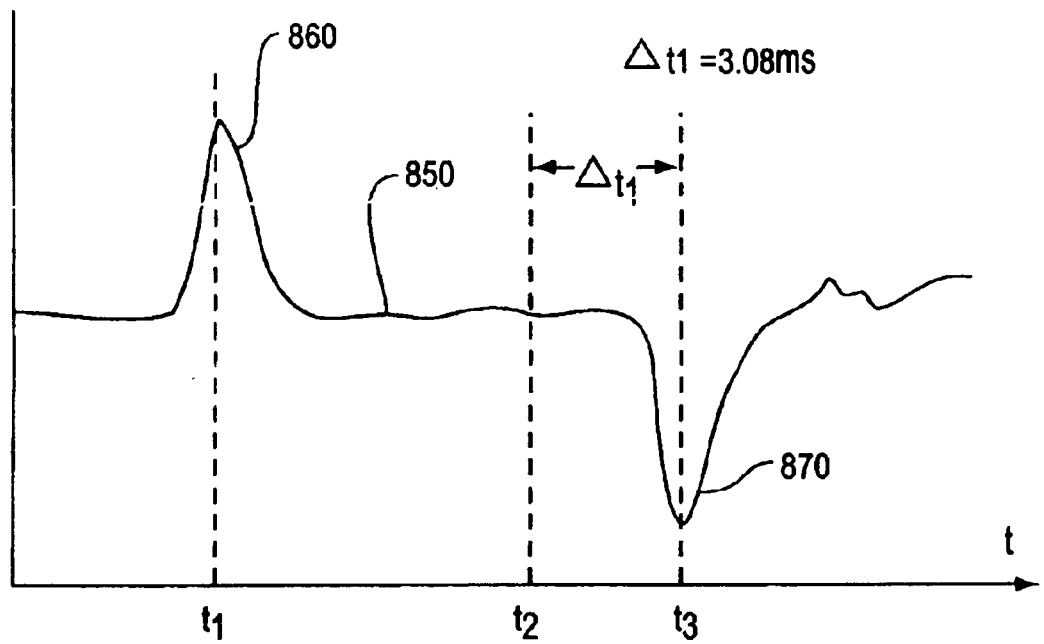
Figure 11:
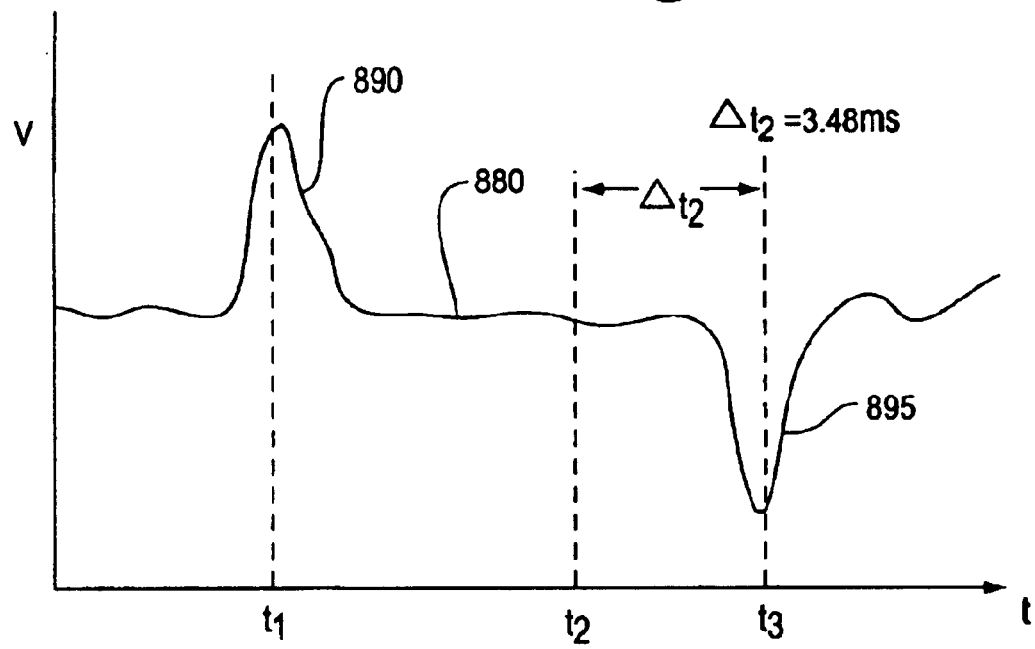

A second more particular method of calculating the dielectric constant of product 14, with the relationship of Equation 2, uses threshold controller 230 to calculate a time delay between transmission of the transmit pulse and reflection of the pulse from surface 128. More particularly, the method calculates a time of travel of the microwaves through a known distance of product 14. The method is shown in the plots of FIGS. 10 and 11 and is summarized in the flow diagram of FIG. 12. Those skilled in the art will recognize that the waveforms shown in FIGS. 10 and 11 can be inverted without departing from the spirit and scope of the invention.

The method begins at block 805 with generation of the transmit pulse. The transmit pulse is transmitted along the termination into products 14 and 15. At block 810, the first reflected wave pulse is received and detected with the threshold controller. Receipt of the first reflected wave pulse starts a clock or designates the beginning of a time period as shown at block 815. Next, the second reflected wave pulse is received and detected at block 820. Receipt of the second reflected wave pulse designates the end of the time period, as shown at block 825 where the time period is recorded. At block 830, the dielectric constant of product 14 is calculated as a function of the recorded time period which is indicative of a time of travel of the microwaves along the termination a known distance through product 14.

Figure 12:
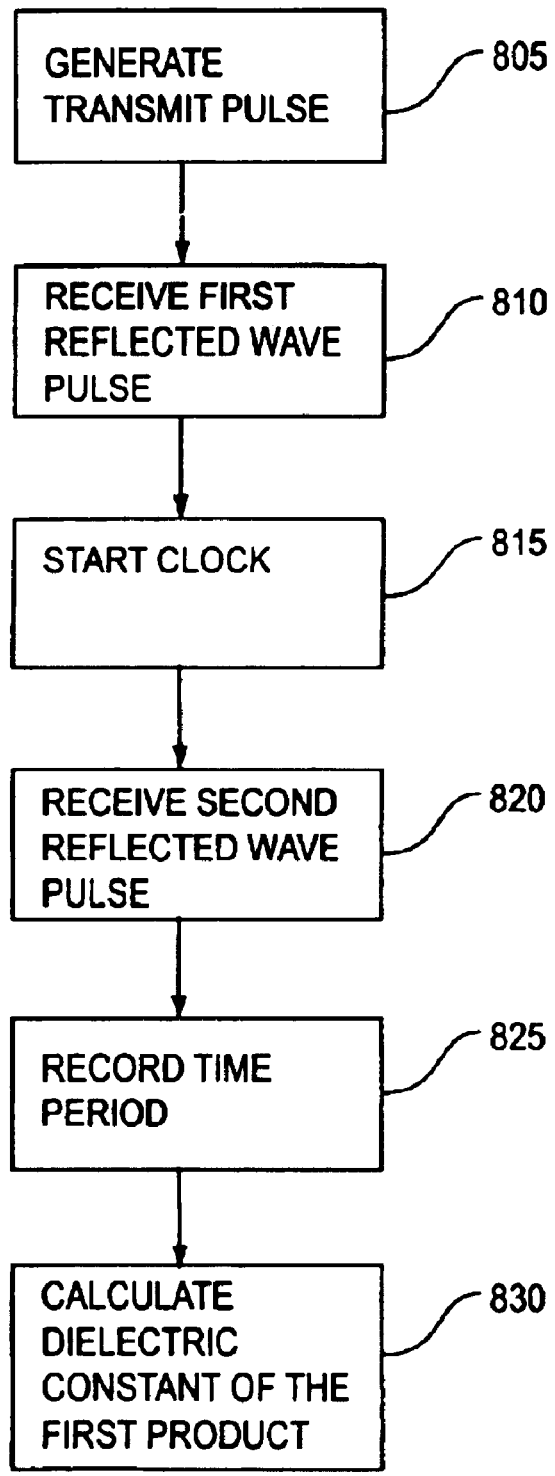

FIGS. 10 and 11 illustrate the method of FIG. 12. FIGS. 10 and 11 illustrate equivalent time LPTDRR waveforms 850 and 880 corresponding to representations of first and second products filling different tanks, with the first and second products having first and second dielectric constants, respectively. In both plots, the product either substantially covers the leads of termination 110, or covers them by a known distance.

As can be seen in FIGS. 10 and 11, the time delay between the transmitted pulses (represented by fiducial pulses 860 and 890) and the reflected pulses 870 and 895 (corresponding for example to reflections off of the bottom of tank 12 or termination 110 or to reflections at a product-to-product interface) varies from one material to the next. This variation is due to the different dielectric constants of the materials. This is further illustrated by time differences $\Delta_{t1}$ and $\Delta_{t2}$, which represent the time required for microwaves to travel the same sample distance in each of the two materials. In the material having the first dielectric constant, the time required to travel the sample distance was 3.08 ms, while in the material having the second dielectric constant, the time required to travel the same sample distance was 3.48 ms. Thus, the time delay between transmission of the microwave signal and the reflection off of an interface a known distance down the termination can be used to calculate the dielectric constant.

In one embodiment, the present invention can be used to measure the concentration of a material in a process fluid. For example, it is desirable to measure the concentration of a material carried in process fluid which flows through pipe 914. In a specific example, it is desirable to measure the percentage concentration of water in a natural gas flow line or the amount of water in a steam flow line (known as "steam quality"). Steam quality is an especially important parameter to measure because it relates directly to the amount of thermal energy carried by a steam line. For example, steam at 400° F. of 50% qualities carries less energy than steam at 400° F. of 100% quality. In applications in which delivery of large quantities of energy is required, such as steam flooding of an oil field for purposes of enhanced oil recovery, the steam quality must be known such as that the amount of energy injected into the oil field can be controlled.

According to one embodiment, microwave radiation is directed through a process fluid by an antenna that is in direct contact with the fluid. The relative concentration of a material in the fluid causes a change in the dielectric constant of the fluid. This change in the dielectric constant in turn causes a change in the time of flight of the reflected microwave pulse, and also a change in the energy level of the reflected pulse. Either or both the time of flight and the reflected energy level can be measured by detection circuitry and can be correlated to the concentration of a material in the process fluid. This can be done by establishing a relationship either theoretically or through testing, between the amplitude change or time delay of the return pulse and the material concentration. One advantage of this technique is that if the concentration of a material changes slowly, the detection circuitry can integrate the reflected microwave signals over time (either time of flight, peak height or both) to provide a more accurate measurement of the concentration of the particular material.

Placing the contacting antenna in contact with the process fluid allows the fluid to flow over the antenna. A change in the concentration of the material, such as the steam quality, will result in a change in the dielectric. Using the end of the antenna as a target, the dielectric change will cause an apparent shift when measuring the distance (from the antenna connection) to the opposed end of the antenna. A longer contacting antenna will have a larger apparent shift in distance. Therefore, increased sensitivity can be obtained by increasing the length of the contacting antenna. This distance change is dictated by the following equation:

$$D = (c*t)/(2*\sqrt{\Delta\epsilon_R})$$ EQ. 4 where D is the distance, c is the speed of light, t is the time to target and $\Delta\epsilon_R$ is the dielectric change.

Figure 13:
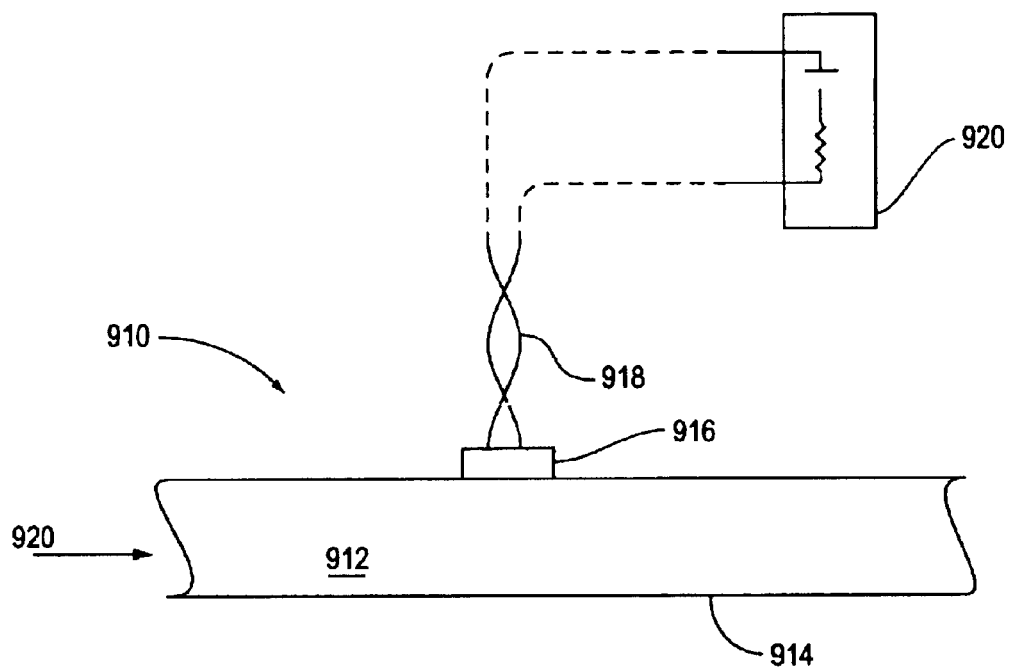
FIG. 13 is a simplified diagram showing a transmitter configured to determine concentration of material.

FIG. 13 is a simplified diagram showing an industrial process 910 in which a process fluid 912 is carried in process piping 914. The present invention can be used with other types of vessels and is not limited to piping 914. A process transmitter 916 operates in accordance with the invention and monitors reflected microwave radiation to determine a characteristic of the process fluid such as the concentration of material in the process fluid 912. Transmitter 916 couples through a process control loop 918, such as a two-wire process control loop, to a control room 920 at a remote location. Control room 920 is modeled as a voltage source in series with a resistance. The process control loop 918 can be in accordance with any communication technique.

Figure 14:
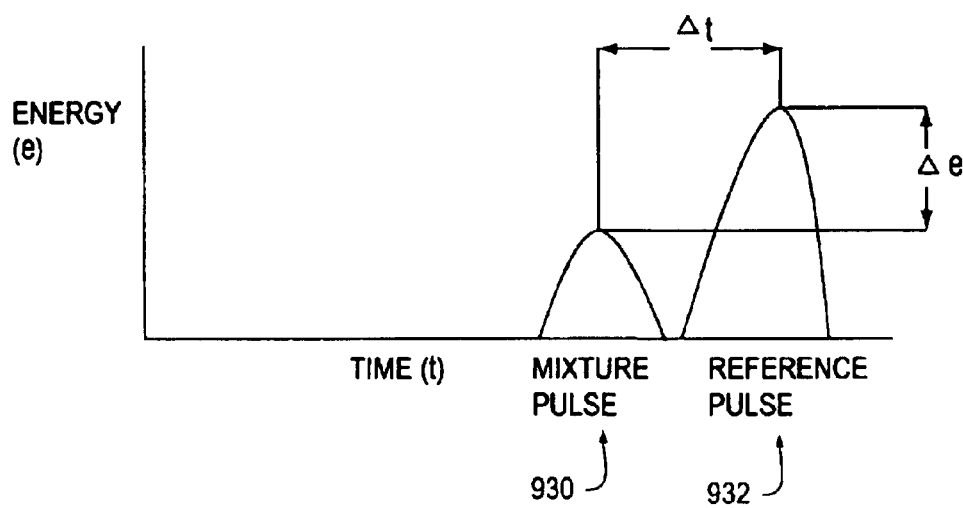
FIG. 14 is a graph of energy versus time showing a mixture pulse and a reference pulse.

FIG. 14 is a graph of energy (e) versus time (t) and shows a reflected or return pulse 930 and a reference or transmit pulse 932. The time difference is illustrated in FIG. 14 as $\Delta t$ and the energy difference between the two signals is illustrated as $\Delta e$. The relationship between the concentration of a material and the time delay or energy difference can be determined either empirically or theoretically. The correlations can also use artificial intelligence techniques including fuzzy logic, neural networks, etc. to establish the relationship. Additionally, the two parameters, $\Delta t$ and $\Delta e$, can be used to verify the measurement.

Figure 15:
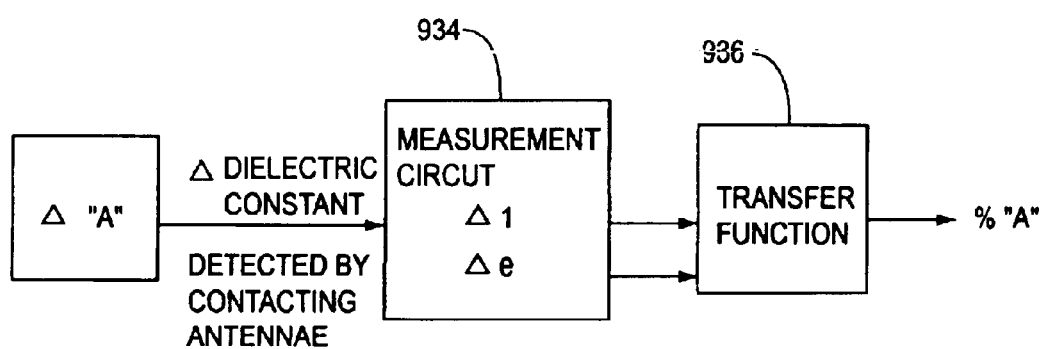
FIG. 15 is a block diagram showing circuitry for calculating a change in concentration of material

FIG. 15 is a simplified block diagram which illustrates the present invention for detecting the concentration of a material "A" in a process fluid. A change in the dielectric constant of the process fluid is detected by a contacting antenna. Measurement circuitry 934 measures $\Delta t$ and/or $\Delta e$. A transfer function 936 is used to correlate one or both of these parameters to a percentage or concentration of the material "A" in the process fluid.

Figure 16:
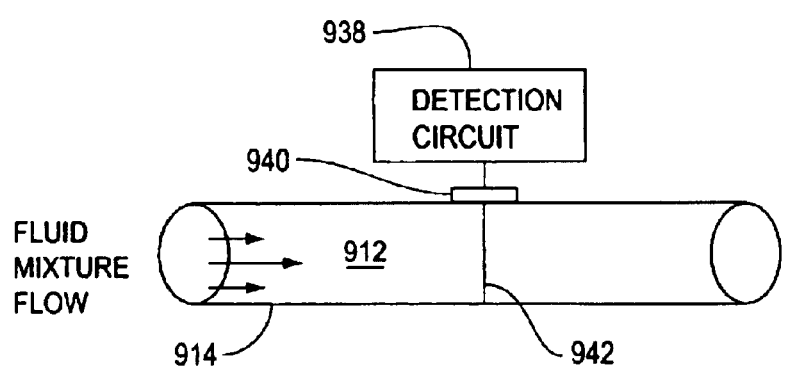
FIG. 16 is a simplified diagram showing a contacting antenna in a process fluid flow.

FIG. 16 is a simplified diagram showing detection circuitry coupled to a contacting antenna 942 in process piping 914 through a process seal 940. The detection circuitry can be, for example, transmitter 916 shown in FIG. 13.

Figure 17:
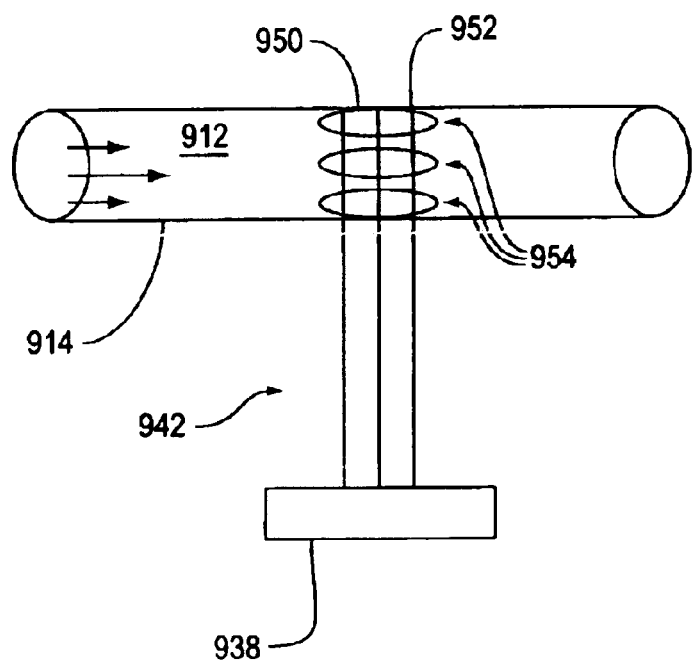
FIG. 17 is a simplified diagram of concentration detecting circuitry of the invention using a pitot tube as an antenna.

FIG. 17 shows another example embodiment in which an averaging pitot tube is used as microwave antenna 942. An averaging pitot tube includes a high side plenum 950 and a low side plenum 952. The flow through pipe 914 causes a pressure differential between the plenums which can be correlated to flow rate using known techniques. The metal pitot tube can be used to carry a microwave pulse 954. In this embodiment, the microwave pulse 954 propagates as an annular wave through the process fluid around the pitot tube.

Figure 18:
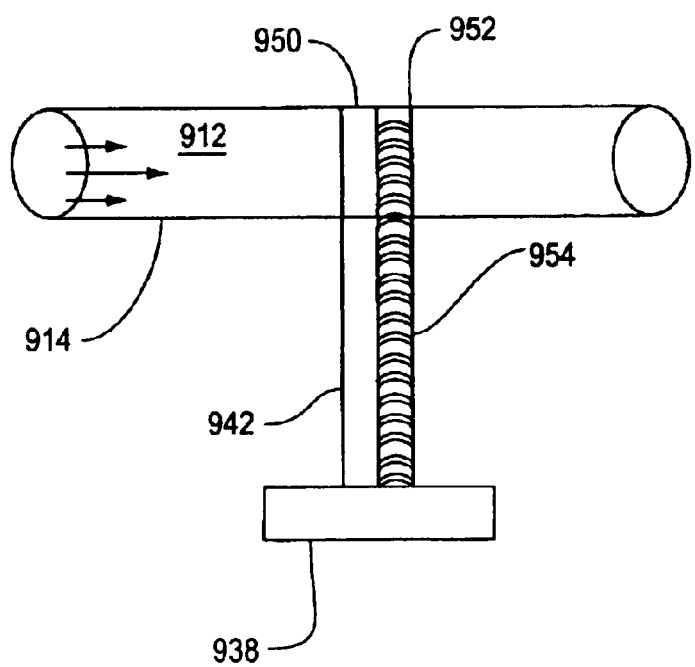
FIG. 18 is a diagram in which the microwave signal is carried along an interior plenum of the pitot tube.
Figure 19:
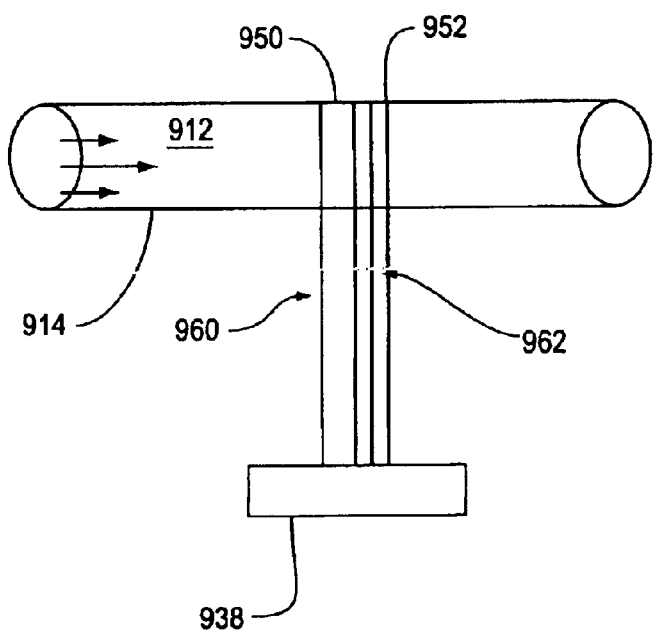
FIG. 19 is a simplified diagram in which an antenna is carried within the plenum of the pitot tube.

In an alternative embodiment illustrated in FIG. 18, the microwave pulse 954 is carried along the interior of a plenum, for example the low side plenum 52. The plenum is assumed to be in intimate contact with the process fluid to be measured. In the embodiment of FIG. 19, an antenna 962 is carried in one of the plenums of pitot tube 960.

Figure 20:
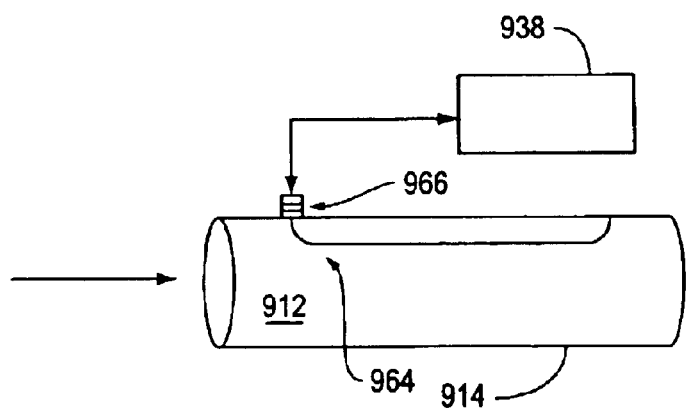
FIG. 20 is a diagram showing an antenna which extends parallel with the direction of flow of process fluid.

FIG. 20 shows another embodiment of the present invention in which an antenna 964 extends substantially along the direction of the flow through process piping 914. The antenna 964 couples to the transmitter 938.

Figure 21:
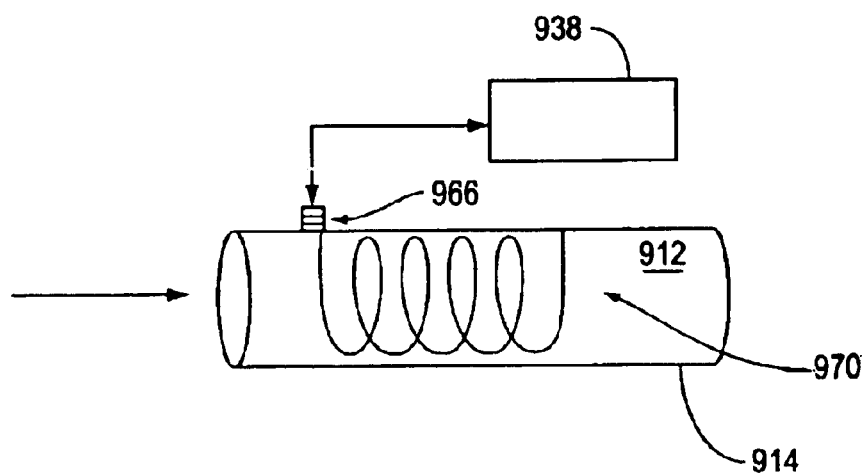
FIG. 21 shows an embodiment in which a helical antenna is used.

FIG. 21 shows an embodiment in which a helical antenna 970 is used to thereby increase the length of the antenna. The increased antenna length provides increased sensitivity to changes in the dielectric constant of the process fluid 912. Other shapes can be used and the invention is not limited to the helical shape shown in FIG. 22.

Figure 22:
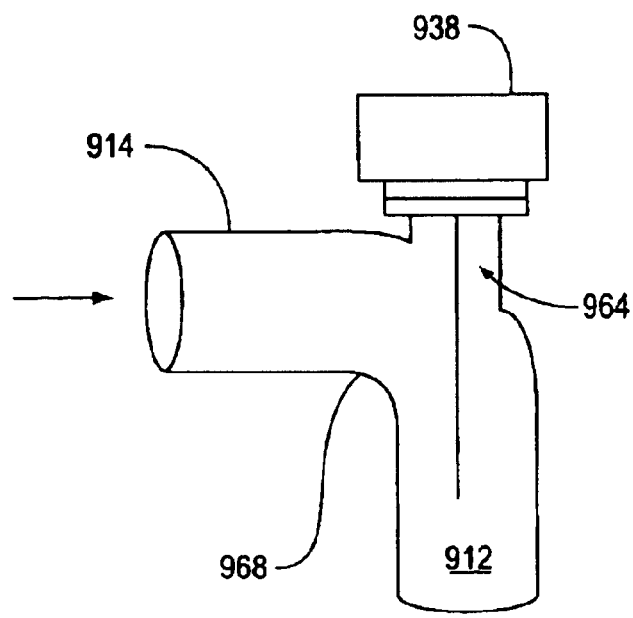
FIG. 22 shows an embodiment in which process piping includes an elbow and a portion of the antenna extends in the direction of flow.

FIG. 22 shows another example embodiment in which piping 914 includes an elbow 968 and antenna 964 is arranged such that a portion extends in the direction of the flow. If the antenna extends along the direction of flow, the amount the flow is obstructed is minimized.

Figure 23:
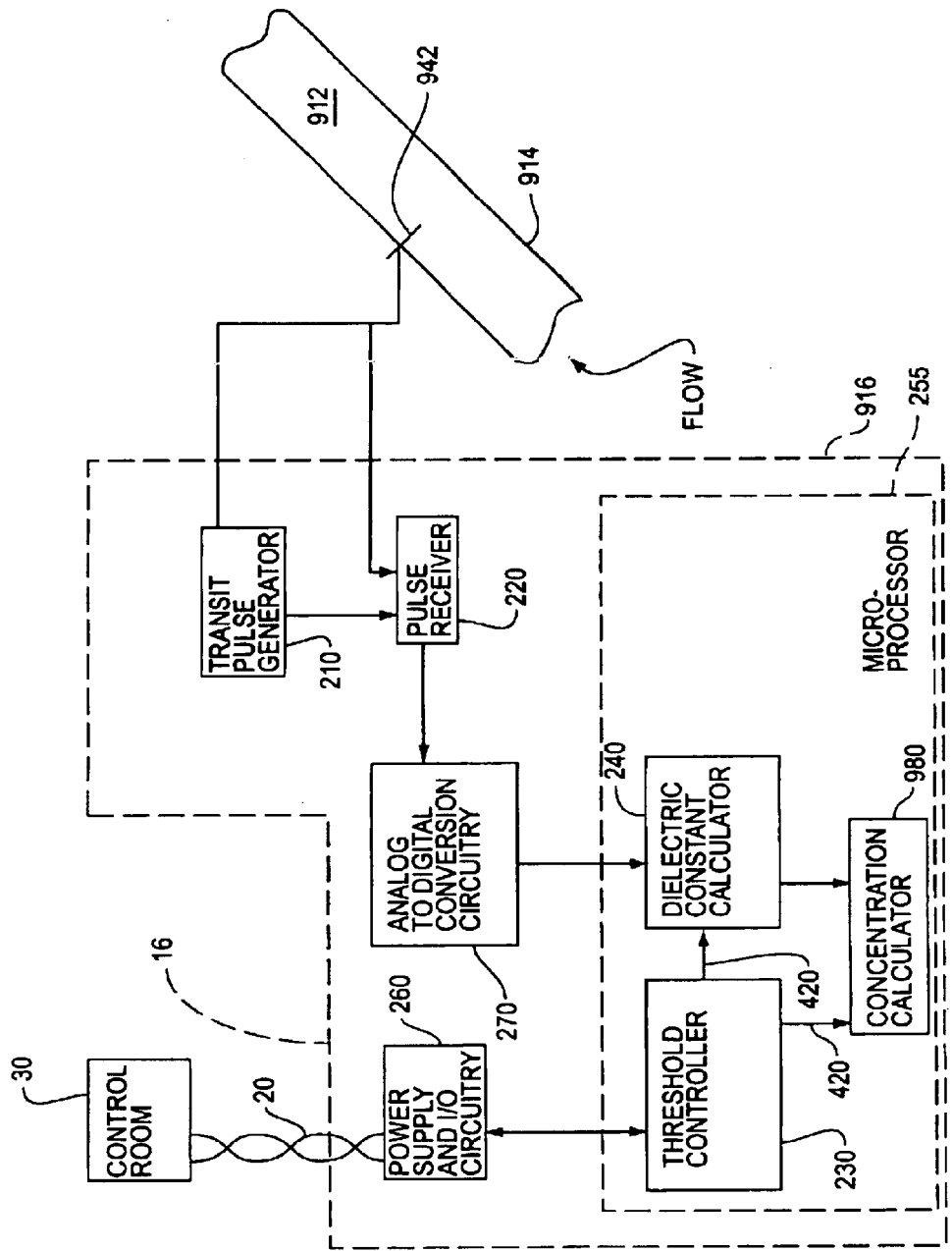
FIG. 23 is a block diagram of a transmitter configured to determine material concentration.

FIG. 23 is a block diagram of transmitter 916 configured to determine the concentration of a material in process fluid 912. FIG. 23 is similar to FIG. 3 and similar numbers are used. A concentration calculator 980 is configured to correlate the time delay or reflected energy change of the return microwave signal to material concentration. Note that the actual implementation may not include dielectric constant calculator 240 and the time delay and/or change in signal strength can be used to directly determine material concentration.

Although the present invention has been described with reference to preferred embodiments, workers skilled in the art will recognize that changes may be made in form and detail without departing from the spirit and scope of the invention. For example, the above described methods of calculating dielectric constants can be combined to aid in calculating multiple dielectric constants, or to provide a more accurate calculation of dielectric constants. The invention can be used in fluid flow, stream, or with substantially static process fluid. As used herein, process fluid includes liquids, gases, foam, etc., their combinations, and/or solid material carried by such substances. The material can be in liquid gaseous or particulate form.

What is claimed is:

1. A process transmitter for concentration of a material in a process fluid, comprising
   an antenna configured to contact the process fluid;
   a pulse generator coupled to configure the antenna to generate a microwave transmit pulse through the antenna;
   a pulse receiver coupled to the antenna configured to receive a reflected, pulse from the antenna;
   a concentration calculator configured to calculate the concentration of the material as a function of the reflected pulse; and
   a connection configured to couple to a two wire process control loop and to carry information related to the concentration of the material and provide power to completely power the process transmitter.

2. The apparatus of claim 1 wherein the concentration of the material is calculated as a function of a time delay of the return pulse.

3. The apparatus of claim 1 wherein the concentration of the material is calculated as a function of an energy level of the return pulse.

4. The apparatus of claim 1 wherein the antenna comprises a pitot tube.

5. The apparatus of claim 4 wherein pulses are carried along an exterior of the pitot tube.

6. The apparatus of claim 4 wherein pulses are carried along an interior of the pitot tube.

7. The apparatus of claim 1 wherein the antenna extends in a direction of a flow of the process fluid.

8. The apparatus of claim 1 wherein the antenna is curved.

9. The apparatus of claim 6 wherein the antenna is helical.

10. A method of determining the concentration of a material in a process fluid by a process transmitter, comprising:
    transmitting a microwave pulse along an antenna which contacts the process fluid;
    receiving a reflected microwave pulse from the antenna in response to the transmitter pulse;
    calculating concentration of the material in the process fluid as a function of the reflected pulse;
    providing an output to a two wire process control loop related to the concentration of material; and
    completely powering the process transmitter with power received from the two wire process control loop.

11. The method apparatus of claim 10 wherein the concentration of the material is calculated as a function of a time delay of the return pulse.

12. The method of claim 10 wherein the concentration of the material is calculated as a function of an amplitude of the return pulse.

13. The method of claim 10 wherein the antenna comprises a pitot tube.

14. The method of claim 13 wherein pulses are carried along an exterior of the pitot tube.

15. The method of claim 13 wherein pulses are carried along an interior of the pitot tube.

16. The method of claim 13 including calculating a dielectric constant of the process fluid.

17. The method of claim 10 wherein the antenna extends in a direction of a flow of the process fluid.

18. The method of claim 10 wherein the antenna is curved.

19. The method of claim 18 wherein the antenna is helical.

* * * * *